United States Patent [19]
Grunicke et al.

[11] Patent Number: 5,770,593
[45] Date of Patent: Jun. 23, 1998

[54] METHOD OF DETERMINING A PHARMACEUTICAL COMBINATION PREPARATIONS FOR USE IN ANTI-NEOPLASTIC THERAPY

[75] Inventors: Hans Hermann Grunicke, Mils, Austria; Dieter Herrmann, Heidelberg, Germany; Johann Hofmann, Scharnitz, Austria; Elmar Bosies, Weinheim, Germany

[73] Assignee: Boehringer Mannheim GmbH, Mannheim, Germany

[21] Appl. No.: 464,343

[22] Filed: Jun. 5, 1995

Related U.S. Application Data

[62] Division of Ser. No. 319,478, Oct. 7, 1994, Pat. No. 5,578,590, which is a division of Ser. No. 759,201, Sep. 11, 1991, abandoned, which is a continuation of Ser. No. 395,698, Aug. 18, 1989, abandoned.

[30] Foreign Application Priority Data

Aug. 18, 1988 [DE] Germany ............ 38 27 974.6

[51] Int. Cl.$^6$ ............ A61K 31/545; A61K 31/55; A61K 31/70; A61K 31/35
[52] U.S. Cl. ............ 514/200; 514/211; 514/50; 514/456; 514/731; 514/736; 424/649
[58] Field of Search ............ 514/200, 211, 514/50, 456, 731, 736; 424/649

[56] References Cited

PUBLICATIONS

O'Brian et al., J. Natl. Cancer Inst., vol. 80(20), pp. 1628–1633, 1988 (abstract).
Hannun et al, J. Biol. Chem., vol. 263 (11), pp. 5124–5133, 1988. (abstract).
Satyamoorthy et al., Proc. Am Assoc. Cancer Res. Anau. Mect, vol. 30 (0), p. 216, 1989.
Chemical Abstracts, Band 94, 1981, Seite 62 Zusammenfassung Nr. 114601t, Columbus, Ohio, US; M. Sluyser Et Al.: "Combined endocrine therapy and chemotherapy of mouse mammary tumors", & Eur. J. Cancer 1981, 17(2), 155–9 *Zusammenfassung*.
Chemical Abstracts, Band 100, 1984, Seite 33, Zusammenfassung Nr. 132230t, Columbus, Ohio, US; C. Benz et al.: "tamoxifen and 5–fluorouracil in breast cancer: cytotoxic synergism in vitro", & Cancer Res. 1983, 43(11), 298–303 *Zusammenfassung*.
Chemical Abstract, Band 105, 1986 Seite 25 Zusammenfassung Nr. 202832v, Columbus, Ohio, US; V.V. Fomina et al.: "New ways to improve the efficacy of tamoxifen in the treatment of mammary cancer", & Izv. Akad. Nauk Kaz. SSR, Ser Biol. 1986, (4) 67–70 *Zusammenfassung*.
Chemical Abstracts, Band 98, 1983, Seite 34, Zusammenfassung Nr. 119268G, Columbus, Ohio, US; L.D. Morris et al.: "Adjuvant treatment with adramycin, methotrexate and tamoxifen of DMBA induced tumors in the rat", & IRCS Med. Sci.: Libr. Compend. 1982, 10 (12), 1045 *Zusammenfassung*.

Dialog 07028115, Medline 89330115; J. Hofmann: "Syneroistic annancement of the antioroliferative activity of cois-–diamminedichlorplatinum (II) by the ether lipid analogue BM41440, aninhibitor if protein kinase C", & Lipids Apr. 1989, Band 24, Nr. 4, Seiten 312–317 *Insgesamt*.
Chemical Abstracts, Band 109, 1988, Seite 29, Zusammenfassung Nr. 204527f, Columbus, Ohio, US; J. Hofman et al.: "Enhancement of the antiproliferative effect of cis–diamminedichloroplatinum(II) and nitrogen mustard by inhibitors of protein kinase C", & Int. J. Cancer 1988, 42(3), 382–8 *Zusammenfassung*.
Sluyser et al. "Combined Endocrine Therapy and Chemotherapy of Mouse Mammary Tumors", vol. 17, p. 155 Eur. J. Cancer, 1981.
Benz et al. "Tamoxifen and 5–Fluorouracil in Breast Cancer: Cytotoxic Synergism In Vitro" vol. 43, p. 5293 Cancer Res., 1983.
Fomina et al. "New Ways to Improve the Efficacy of Tamoxifen in the Treatment of Mammary Cancer", vol. 4, p. 67 Izv. Akad. Nauk. Kaz. SSR, Ser. Biol., 1986.
Morris et al. "Adjuvant Treatment with Adriamycin, Methotrexate and Tamoxifen of DMBA Induced Tumors in the Rat" vol. 10 page 1045t. IRCS Med. Sci.: Libr. Compend., 1982.
Hofmann et al. "Synergistic Enhancement of the Antiproliferative Activity of cis–Diamminedichloroplatinum(II) by the Ether Lipid Analogue BM 41.440, an Inhibitor of Protein Kinase C", vol. 24, p. 312 Lipids, 1989.
Hofmann et al. "Enhancement of the Antiproliferative Effect of cis–Ciamminedichloroplatinium(II) and Nitrogen Mustard by Inhibitors of Protein Kinase C" vol. 42, p. 382 Int. J. Cancer, 1988.
Palayoor et al. "Inhibition of Protein Kinase C by Antineoplastic Agents: Implications for Drug Resistance", vol. 148, p. 718 Biochem. Biophys. Res. Commun., 1987.
Ido et al. "An Inhibitor of Protein Kinase C, 1–(5–Isoquinolinylsulfonyl)–2–Methylpiperazine (H–7) Inhibits TPA–Induced Reduction of Vincristine Uptake from P388 Murine Leukemic Cell", vol. 10, p. 1063 Leukemia Res., 1986.
Laubenstein et al. "Treatment of Epidemic Kaposi's Sarcoma with Etoposide or a Combination of Doxorubicin, Bleomycin and Vinblastine", vol. 2, p. 1115 J. Clin. Oncol., 1984.
Kaplan et al. "Treatment of Kaposi's Sarcoma in Acquired Immunodeficiency Syndrome with an Alternating Vincristine–Vinblastine Regimen", vol. 70, p. 1121 Cancer Treat. Rep., 1986.

(List continued on next page.)

*Primary Examiner*—Chhaya D. Sayala
*Attorney, Agent, or Firm*—Nikaido Marmelstein Murray & Oram

[57] ABSTRACT

The present invention provides a pharmaceutical combination preparation, wherein it contains at least two active materials, the first active material being an inhibitor of protein kinase C and the other active material having an anti-neoplastic action, as well as pharmacologically acceptable carriers and adjuvants.

10 Claims, No Drawings

OTHER PUBLICATIONS

Giaccone et al. "Mitomycin C, Vinblastine and cis–platin. An Active Regimen for Advanced Non–Small Cell Lung Cancer", vol. 56, p. 475 Brit. J. Cancer, 1987.

Olweny et al. "Treatment of Kaposi's Sarcoma by Combination of Actinomycin–D, Vincristine and Imidazole Carboxamide (NSC–45388): Results of a Randomized Clinical Trial", vol. 14, p. 649 Int. J. Cancer, 1974.

Nathanson et al. "Vinblastine, Infusion, Bleomycin and cis–Dichlorodiammine–Platinum Chemotherapy in Metastic Melanoma", vol. 48, p. 1290 Cancer, 1981.

Chahinian et al. "MACC(Methotrexate, Adriamycin, Cyclophosphamide and CCNU) in Advanced Lung Cancer", vol. 43, p. 1590 Cancer, 1979.

Buyukpamakcu et al. "Combined Chemotherapy in 76 Children with Non–Hodgkin's Lymphoma Excluding Burkitt's Lymphoma", vol. 56, p. 625 Br. J. Cancer, 1987.

Corbett et al. "Biology and Therapeutic Response of Mouse Mammary Adenocarcinoma (16/C) and its Potential as a Model for Surgical Adjuvant Chemotherapy" vol. 62, p. 1471 Cancer Treat. Rep., 1978.

Wallach et al. "Chemotherapy of Recurrent Ovarian Carcinoma with cis–Dichlorodiammine Platinum II and Adriamycin" vol. 55, p. 371 Obstet. Gynecol., 1980.

Anderson et al. "Childhood Non–Hodgkin's Lymphoma. The Results of Randomized Therapeutic Trial Comparing a 4–Drug Regimen (COMP) with a 10–Drug Regimen ($LSA_2-L_2$)", vol. 308, p. 559 New Eng. J. Med., 1983.

Vogel et al. "Treatment of Kaposi's Sarcoma with a Combination of Actinomycin D and Vincristine", vol. 31, p. 1382 Cancer, 1973.

Cohen et al. "Combination Chemotherapy of Malignant Melanoma with Imidazole Carboxamide, BCNU and Vincristine", vol. 39, p. 41 Cancer, 1977.

Bailey et al. "Chemotherapy of Human Breast–Carcinoma Xenografts", vol. 42, p. 530 Br. J. Cancer, 1980.

DeWasch et al. "Combination Chemotherapy with Three Marginally Effective Agents, CCNU, Vincristine and Bleomycin, in the Treatment of Stage III Melanoma", vol. 60, p. 1273 Cancer Treat. Rep., 1976.

Holland et al. "Cisplatin Therapy of Ovarian Cancer", pp. 383–391 in Cisplatin, 1980, Academic Press.

Nathanson et al. "Pilot Study of Vinblastine and Bleomycin Combinations in the Treatment of Metastatic Melanoma", vol. 64, p. 133 Cancer Treat. Rep., 1980.

Schulman et al. "Phase II Trial of Mitomycin, Vinblastine and Cisplatin (MVP) in Non–Small Cell Bronchogenic Carcinoma" vol. 67, p. 943 Cancer Treat. Rep., 1983.

Mabel et al. "Combination Chemotherapy Against B16 Melanoma: Bleomycin/Vinblastine, Bleomycin/Cis–Diamminedichloroplatinium, 5–Fluorouracil/BCNU and 5–Fluorouracil/Methyl–CCNU", vol. 42, p. 1711 Cancer, 1978.

Samuels et al. "Bleomycin Combination Chemotherapy in the Management of Testicular Neoplasias", vol. 36, p. 318 Int. J. Cancer, 1975.

Ettinger et al. "Adriamycin (ADR) and Cis–Diamminedichloroplatinum (DDP) as Adjuvant Therapy in Osteosarcoma of the Extremities" abstract C–292 Proc. Amer. Assoc. Cancer Res. and ASCO, 1980.

Pendergrass et al. "Intensive Timed Sequential Combination Chemotherapy and Adjunctive Radiotherapy in Extensive Stage Small Cell Carcinoma of the Lung (SCC)", abstract C–505 Proc. Amer. Assoc. Cancer Res. and ASCO, 1980.

Mason et al. "Mitomycin (M), Vinblastine (V) and Cisplatin (P) Combination Chemotherapy in Non–Small Cell Lung Cancer (NSCLC)", abstract C–507 Proc. Amer. Assoc. Cancer Res. and ASCO, 1980.

Livingston et al. "BACON (Bleomycin, Adriamycin, CCNU, Oncovin and Nitrogen Mustard) in Squamous Lung Cancer" vol. 37, p. 1237 Cancer, 1976.

Vogl et al. "Combination Chemotherapy with Adriamycin and Cis–Diamminedichloroplatinum in Patients with Neoplastic Diseases", vol. 38, p. 21 Cancer, 1976.

Bitran et al. "Cyclophosphamide, Adriamycin, Methotrexate and Procarbazine (CAMP)–Effective Four–Drug Combination Chemotherapy for Metastatic Non–Oat Cell Bronchogenic Carcinoma", vol. 60, p. 1225 Cancer Treat. Rep., 1976.

Okazaki et al. "Staurosporine, a Novel Protein Kinase Inhibitor, Enhances HL–60–cell Differentiation Induced by Various Compounds", vol. 16, p. 42 Exp. Hematol., 1988.

Britell et al. "cis–Dichlorodiammineplatinum(II) Alone Followed by Adriamycin Plus Cyclophosphamide at Progression Versus cis–Dichlorodiammineplatinum(II), Adriamycin and Cyclophosphamide for Adenocarcinoma of the Lung", vol. 62, p. 1207 Cancer Treat. Rep., 1978.

Bruckner et al. "Combination Chemotherapy of Ovarian Carcinoma with Cyclophosphamide, Adriamycin and cis––Dichlorodiammineplatinum(II) After Failure of Initial Chemotherapy", vol. 62, p. 1021 Cancer Treat. Rep., 1978.

Spigel et al. "Vinblastine (NSC–49842) and Bleomycin (NSC–125066) Therapy for Disseminated Testicular Tumors" vol. 58, p. 213 Cancer Chemotherapy Rep., 1974.

Moertel et al. "Brief Communication: Therapy of Advanced Colorectal Cancer with a Combination of 5–Fluorouracil, Methyl–1,3–cis(2–chlorethyl)–1–nitrosourea and Vincristine)", vol. 54, p. 69 J. Natl. Cancer Inst., 1975.

Livingston et al. "Kinetic Scheduling of Vincristine (NSC–67574) and Bleomycin (NSC–125066) in Patients with Lung Cancer and Other Malignant Tumors" vol. 57, p. 219 Cancer Chemotherapy Rep., 1973.

Einhorn et al. "Combination Chemotherapy of Disseminated Testicular Carcinoma with cis–Platinum Diammine Dichloride (CPDD), Vinblastine (VLB) and Bleomycin (BLEO)", vol. 17, p. 240, abstract C–13 Proc. Amer. Assoc. Cancer Res., 1976.

Holoye et al. "Cytoxan, Adriamycin and Vincristine Combination with Radiation Therapy in the Treatment of Small Cell Carcinoma of the Lung", vol. 16, p. 112 abstract 447 Proc. Amer. Assoc. Cancer Res., 1975.

Eagan et al. "Cytoxan (CTX), Adriamycin (ADR) and Cis–Platinum (CDDP) Infusion (CAP–II) in Patients with Advanced Large Cell (LGC) Lung Cancer" abstract 311 Proc. Amer. Assoc. Cancer Res.,1978.

Vogl et al. "Cyclophosphamide (C), Hexamethylmelamine (H), Adriamycin (A) & Diamminedichloroplatinum (D) as Initial Chemotherapy for Advanced Ovarian Cancer", abstract 181 Proc. Amer. Assoc. Cancer Res., 1978.

Ohnuma et al. "Adriamycin (ADM) and Diamminedichloroplatinum (DDP) in Combination" abstract 1205 Proc. Amer. Soc. Clin. Oncol., 1975.

Chahinian et al. "Chemotherapy of Bronchogenic Carcinoma with Methotrexate (MTX), Adriamycin (ADM), Cyclophosphamide (CYT) and CCNU" abstract C–203 Proc. Amer. Soc. Clin. Oncol., 1976.

Bruckner et al. "Chemotherapy of Ovarian Cancer with Adriamiyin (ADM) and Cis–Platinum (DDP)" abstract C–204 Proc. Amer. Soc. Clin. Oncol., 1976.

Troner et al. "Cyclophosphamide, Adriamycin and Cis–Platinum (CAP) Chemotherapy of Metastatic Transitional Cell Carcinoma (TCC) of the Bladder", abstract 642 Proc. Amer. Assoc. Cancer Res., 1978.

Parker et al. "Adriamycin–Cyclophosphamide Therapy Therapy in Ovarian Cancer" abstract 1171 Proc. Amer. Soc. Clin. Oncol., 1975.

Herman et al. "Combination Chemotherapy with Adriamycin and Cyclophosphamide (With or Without Radiation Therapy) for Carcinoma of the Lung", vol. 61, p. 875 Cancer Treat. Rep., 1977.

Higby et al. "Adriamycin–Cyclophosphamide and Adriamycin–cis–Dichlorodiammineplatinum(II) Combination Chemotherapy in Patients with Advanced Cancer", vol. 61, p. 869 Cancer Treat. Rep., 1977.

Lloyd et al. "Combination Chemotherapy with Adriamycin (NSC–123127) and Cyclophosphamide (NSC–26271) for Solid Tumors: A Phase II Trial", vol. 60, p. 77 Cancer Treat. Rep., 1976.

Weisenthal et al. "Perturbation of In Vitro Resistance in Human Lymphatic Neoplasms by Combinations of Putative Inhibitors of Protein Kinase C", vol. 71, p. 1239 Cancer Treat. Rep., 1987.

METHOD OF DETERMINING A PHARMACEUTICAL COMBINATION PREPARATIONS FOR USE IN ANTI-NEOPLASTIC THERAPY

This is a division of application Ser. No. 08/319,478 filed Oct. 7, 1994, now U.S. Pat. No. 5,578,590 which is a divisional of Ser. No. 07/759,201, filed Sep. 11, 1991, which is a continuation of Ser. No. 07/395,698, both adandoned.

The present invention is concerned with pharmaceutical combination preparations and with the use thereof as anti-neoplastic medicaments.

More particularly, the subject of the present invention are combination preparations which, as active materials, contain compounds which function as inhibitors of protein kinase in combination with anti-neoplastically-active compounds, for example lipids or lipid derivatives, with cytostatically-active compounds or with compounds which function as inhibitors of phospholipases.

In particular, the present invention is concerned with combination preparations of protein kinase C inhibitors with cytostatically-active compounds.

In anti-neoplastic therapy, the use of chemotherapeutics has already long been a recognised and widely used treatment principle. These chemotherapeutics are used in order to destroy malign cells with uninhibited growth behaviour, whereas normal or healthy cells are to be damaged as little as possible. However, as chemotherapeutics there are used almost exclusively cytostatics which, in general, act non-specifically toxically on normal and malign cells and inhibit the growth of the cells. These cytostatics have a very narrow therapeutic breadth of use, which results in serious side effects.

Such side effects include, for example, haemorrhages, nausea, vomiting, dyspnoea, allergies, alopecias, heart muscle damage, heart rhythm disturbances, pericarditis, peripheral and central neuropathies, pain, nepthropathies, stomatitis, diarrhoea, fever, skin changes, infections, heart insufficiencies or changes of the state of consciousness.

Therefore, it is an object of the present invention to increase the action of chemotherapeutics without involving an increase of the toxic effects of these active materials. Medicaments are to be made available which bring about a reduction of the above-mentioned side effects in the case of the treatment with chemotherapeutics. It is thereby an object to increase the therapeutic breadth of use of these chemotherapeutics. In the case of cytostatics, the anti-tumour and anti-proliferative action is to be strengthened so that these cytostatics can be administered in smaller doses and thus a reduction or removal of the side effects brought about by these agents takes place.

Surprisingly, we have now found that compounds which inhibit various types of protein kinase C, in combination with anti-neoplastic active materials, for example with lipids, lipid analogues, cytostatics or inhibitors of phospholipases, exert a synergistic action. In particular, we have found that in the case of the combination with cytostatics, a strengthening of the anti-proliferative and anti-tumour effect occurs.

Thus, according to the present invention, there is provided a pharmaceutical combination preparation, wherein it contains at least two active materials, the first active material being an inhibitor of protein kinase C and the other active material having an anti-neoplastic action, as well as pharmacologically acceptable carriers and adjuvants.

In the meaning of the present invention, by the term "protein kinase C inhibitors" are to be understood those compounds which inhibit calcium- and phospholipid-dependent protein kinase C or the corresponding isoenzymes thereof in cell-free extracts or in intact cells (Nishizuka, Science, 233, 305–312/1986; Nature, 334, 662–665/1988). Such materials can be isolated by conventional processes from natural materials or can also be synthesised. In this sense, the following compounds can, for example, be used: quercetin (3,3',4',5,7-pentahydrdoxyflavone; Horn, F., J. Biochem., 148, 533–538/1985) phorbol esters, for example 12-O-tetradecanoyl-phorbol 13-acetate (TPA; Regazzi, R., Int. J. Cancer, 37, 731–737/1986), tamoxifen (0-Brien et al., Cancer Research, 45, 2462–2465/1985), staurosporin (Tamaoki, T. et al., Biochem. Biophys. Res. Comm., 135, 397–402/1986) and lipid analogues, for example sulphur-containing phospholipids, especially ilmofosin, and lysolecithins, especially ET-18-OCH$_3$. With the help of the general process described in the following Example 1, it can readily be determined experimentally whether a compound acts as an inhibitor of protein kinase C and can be used in the sense of the present invention. Especially preferred protein kinase C inhibitors are ilmofosin and ET-18-OCH$_3$, quercetin, tamoxifen, staurosporin and its chemically modified derivates.

Ilmofosin and processes for the preparation thereof are known from European Patent Specification No. 0,050,327. The compound is there described as Example 33 with the systematic name 3-hexadecyl-mercapto-2-methoxypropanol-1 phosphoric acid mono-choline ester. Ilmofosin belongs to the group of so-called alkyl-lysolecithin derivatives and is known as compound with cancerostatic properties.

ET-18-OCH$_3$, the systematic name of which is 4-hydroxy-7-methoxy-N,N,N-trimethyl-3,5,9-trioxa-4-phosphaheptacosan-1-aminium 4-oxide, is known from Federal Republic of Germany Patent Specification No. 26 19 686. This compound is there described as being an anti-tumour agent.

The anti-neoplastically active group of compounds include, inter alia, lipids and lipid analogues, for example phospholipids, naturally-occurring, as well as synthetic prepared lipids, which contain a phosphate residue. To these belong the glycero- and the sphingo-phosphatides, as well as the derivatives thereof. From the synthetic group of derivatives are to be mentioned especially the following: 1-0-alkylphospholipid derivatives, for example ET-18-OCH$_3$ (Weltzien, H. U. et al. in: Ether Lipids, Biochemical and Biomedical Aspects; ed. Mangold, H. K. and Paltauf, F; pub. Academic Press, New York, 277–308); 1-S-alkylphospholipid derivatives, for example ilmofosin (3-hexadecyl-mercapto-2-methoxy-methylpropyl-1-phosphocholine); alkyl-, alkenyl- and acyl-phosphocholine and ethanol-amine derivatives, for example hexadecylphosphocholine (HPC); and halogenated analogues of alkyl-, alkenyl- and acyl-glycerol derivatives (Brackerts, H., Lipids 22, 897–903/1987).

To the above-mentioned lipids and lipid analogues also belong lipids which contain a carbohydrate group which are referred to as glycolipids. A differentiation is made between cerebrosides and gangliosides. If the galactose residue of a cerebroside is esterified with sulphate, this is called a sulphatide. All sphingosine-containing lipids are placed together as sphingolipids. There are also the neutral lipids, for example triglycerides and cholesterides, as well as the derivatives thereof. In particular, in this group are to be mentioned the O-alkyl and halogenated derivatives of the triacylglycerols,.

Furthermore, the anti-neoplastic active materials also include, in particular, the chemotherapeutics. Amongst these are to be understood in the following substances foreign to the body which are suitable for and are used in order to damage or destroy micro-organisms, parasites (antibiotics) or tumour cells (cytostatics). Cytostatics and the derivatives thereof from the following groups of cytostatics are thereby to be especially mentioned: alkylants, for example cyclophosphamide, chlorarnbucil, melphalan, busulfan, N-lost compounds, mustargen; metal complex cytostatics, for example metal complexes of platinum, palladium and ruthenium, for example cis-diammine-dichloroplatinum (II); antimetabolites, for example methotrexate, 5-fluorouracil, cytorabin; natural materials, for example vinblastine, vincristine, vindesine and the like; antibiotics, for example dactinomycin, daunorubicin, doxorubicin, bleomycin, mitomycin and the like; hormones and hormone antagonists, for example diethylstilboestrol, testolactone, tamoxifen, aminoglutethimide; other compounds, for example hydroxyurea or procarbazine, as well as corticoids, for example prednisolone.

Anti-neoplastic active materials which are especially preferred according to the present invention include platinum complex compounds, for example, cis-dichlorodiammine-platinum (II) and (IV), mustargen and doxorubicin (adriamycin).

The anti-neoplastic active materials also include compounds which inhibit the phospholipases, for example mepacrine (Hofmann, S. L. et al., Arch. Biochem. Biophys., 215, 237–244/1982), anti-phlogistics, for example indomethacin and the like, neomycin, psychopharmaceuticals, trifluoroperazine and the like.

In special cases, it can also happen that a compound not only falls within the group of already known anti-neoplastic active materials in the meaning of the present invention but can also be assigned to the group of protein kinase C inhibitors. This is, for example, the case with ilmofosin and ET-18-OCH$_3$. However, this does not exclude the possibility of combination with other anti-neoplastic active materials so long as at least one of the active material functions as a protein kinase C inhibitor.

The use of a combination therapy with help of the pharmaceutical preparations of the present invention offers the advantage of the synergistic strengthening of the anti-tumour action of the individual substances. The possibility of the reduction of the doses and thus of the toxicities of the individual substances in the case of simultaneous maintenance of the anti-tumour effectiveness of the combination of the individual substances is thereby provided for. Furthermore, a combination therapy of the above-mentioned individual therapy principles offers the possibility of overcoming cytostatic resistances, which includes not only substance group resistances but also multiple resistances (pleiotropic cytostatic resistance).

In the case of the use of the combination therapy, it is possible to administer the active materials in a so called fixed combination, i.e. in a single pharmaceutical formulation which contains both active materials or to choose a so called free combination in which the active materials, in the form of separate pharmaceutical formulations, can be administered simultaneously or also successively. Such combination preparations can be prepared according to known processes which are usual in galenical technology.

If the active materials are solids, then the active materials can be worked up by usual processes to give solid medicament preparations (tablets, pellets, compresses, gelatine capsules), for example by mixing both active materials with one another and, together with usual carrier and adjuvant materials, pressing to give, for example, tablets. however, it is also possible to make the active materials available, together with appropriate pharmaceutical adjuvants, separate from one another in packing units ready for sale, the packing unit thereby containing the two active materials in separate pharmaceutical formulations.

If the active materials are made available in the form of injection solutions, then these can contain the active material combinations in question in lyophilised form or already in final injectably dissolved form. However, in principle, it is also possible to make available a parenteral formulation for each active material in question in a packing unit so that the injection solutions can possibly be administered separately from one another. In the case of incompatibilities of the active materials with one another, this form of use is the preferred method.

In the case of the parenteral form of administration, the active materials can also be present in substance, possibly together with usual pharmaceutical adjuvant materials, for example in lyophilised form, which can be reconstituted or solubilised by the addition of conventional pharmaceutical injection media.

The pharmaceutical preparations are administered enterally or parenterally in liquid or solid form. All conventional forms of administration can thereby be used, for example tablets, capsules, dragees, syrups, solutions and suspensions. As injection medium, it is preferred to use water which contains the additives usual in the case of injection solutions, such as stabilising agents, solubilising agents and buffers. Additives of this kind include, for example, tartrate and citrate buffers, ethanol, complex formers, for example ethylenediamnine-tetraacetic acid and the non-toxic salts thereof, as well as high molecular weight polymers, such as liquid polyethylene oxide, for viscosity regulation. Liquid carrier materials for injection solutions must be sterile and are preferably placed into ampoules. Solid carrier materials include, for example, mannitol, starch, lactose, silicic acids, higher molecular weight fatty acids, such as stearic acid, gelatine, agar-agar, calcium phosphate, magnesium stearate, animal and vegetable fats and solid high molecular weight polymers, such as polyethylene glycols. Compositions suitable for oral administration can, if desired, also contain flavouring and sweetening materials.

The dosaging can depend upon various factors, such as the mode of administration, species, age and individual state. The doses to be administered daily are about 0.05 to 100 mg./kg. body weight per individual component. In the case of a combination comprising cis-DDP and quercetin, a dosage of, for example, 1–10 mg/kg, especially 3 mg/kg, cis-DDP and 10–50 mg/kg, especially 20 mg/kg, quercetin can be used. The amount of the particular active material per form of administration can be from 5 to 1000 mg.

In the case of the combination preparations, the ratio between the active materials functioning as inhibitors of protein kinase C and the lipids, lipid analogues, cytostatics or inhibitors of phospholipases can vary within a very wide range. Thus, for example, molar ratios of from 1:1000 to 1000:1 are possible, depending upon the effectiveness of the active materials in question. In the case of a combination with cytostatics, a ratio of from 1:100 to 100:1 is preferred. In particular, in the case of the combination of ilmofosin or ET-18-OCH$_3$ with cis-diammine-dichloroplatinum (II), a ratio of from 1:50 to 50:1 can be used but preferably of from 1:1 to 50:1.

In the meaning of the present invention, the following combination preparations can be mentioned by

| protein kinase C inhibitor A | anti-neoplastic compound B | molar ratio A:B |
| --- | --- | --- |
| quercetin | cis-DDP | about 100:1 |
| quercetin | mustargen | about 800:1 |
| tamoxifen | cis-DDP | about 10:1 |
| staurosporin | cis-DDP | about 1:100 |
| ilmofosin | cis-DDP | about 10:1 |
| ET-18-OCH$_3$ | cis-DDP | about 10:1 |

The following Examples demonstrate the synergistic action of some representative combination preparations and exemplify the principles of the present invention.

EXAMPLE 1

General process for investigating compounds with regard to their function as inhibitor of protein kinase C'.

a) Reagents

Horse serum and DMEM (Dulbecco's modified minimal essential medium) were obtained from Boehringer Mannheim GmbH, FRG. Cis-diamminedichloroplatinum (II) was obtained from Homburg Pharma, Frankfurt. [gamma-$^{32}$P]-ATP (10 Ci/mmol) and $^{32}$P-orthophosphate were obtained from Radiochemical Centre, Amersham, U.K.; GF/F filters and DE-52-cellulose were obtained from Whatman, Clifton N.J. (USA), leupeptin, aprotinin, quercetin (3,3',4',5,7-pentahydroxyflavone), tamoxifen, 12-0-tetradecanoylphorbol 13-acetate (TPA), β-glycerophosphate, histone H1 (Type III S), 3-N-morpholino-propane sulphonylic acid (MOPS), L-alpha-phosphatidyl-L-serine and 1,2-sn-diolein were obtained from Sigma, Munchen, FRG, and protein kinase C was obtained from Merck, Darmstadt, FRG. Tris-(hydroxymethyl)-aminomethane (TRIS-HCl), ethyleneglycol-bis-(aminoethyl)-tetraacetic acid (EGTA), sodium dodecyl sulphate (SDS) and Triton X-100 were obtained from Serva, Heidelberg, mustargen (HN2) was obtained from Aldrich, Steinheim and staurosporin originated from Prof. Matter, Ciba-Geigy, Basel, Switzerland.

Ilmofosin was obtained from Boehringer Mannheim GmbH and was synthesised as described by Bosies et al. (Lipids, 22, 947–951/1987). For the investigations, there was used a parent solution of 100 μg./ml. ilmofosin in DMEM+10% foetal calf serum (FCS). The parent solution was stored at 4° C.

Doxorubicin (adriamycin, Adriablastin®) was obtained from Farmitalia/Carlo Erba GmbH, Freiburg, FRG.

b) Inhibition of protein kinase C (PK-C): in vitro method.

Protein kinase C was enriched from Walker cells by chromatography on DEAE-cellulose of the cell extracts by the method described by Kreutter et al. (J. Biol. Chem., 260, 5979–5984/1985). However, to the extracts was additionally added 1 mM phenylmethanesulphonyl chloride, 20 μg./ml. leupeptin and 2 μg./ml. aprotinin. The protein kinase C activity was determined by measurement of the $^{32}$P incorporation of [gamma-$^{32}$P]-ATP into H1 histone according to the method of Fabbro et al. (Arch. Biochem. Biophys., 239, 102–111/1985). The reaction mixture (125 μl) contained 0.5 μCi [gamma-$^{32}$P]-ATP, 40 mM Tris-HCl (pH 7.4), 1 mM calcium chloride, 700 μM EGTA, 50 μg. histone, 6.75 μg. L-alpha-phosphatidyl-L-serine and 0.675 μg. 1,2-s,n-diolein. The reaction time was 10 minutes at 32° C. The enzyme reaction was stopped by the addition of 1 ml. 20% trichloroacetic acid (w/v). The protein was precipitated out on Whatman GF/F filter paper and counted with the help of a liquid scintillation counter.

c) Inhibition of protein kinase C' (PK-C')—in vivo method—Phosphorylation of ribosomal protein S6.

Cells were cultured in DMEM with 0.5% horse serum (v/v) over a period of time of 15 hours and then incubated in phosphate-free medium. After 1 hour, 4 μCi/ml. $^{32}$P-orthophosphate and, after a further 30 minutes, 0.5 μM TPA (12-0-tetradecanoylphorbol 13-acetate) and 50 μM quercetin were added thereto. The cells were lysed in 50 mM Tris-HCl (pH 7.5), 25 mM potassium chloride, 5 mM magnesium chloride, 0.33M saccharose, 1% Triton X-100 (v/v), 1 mM phenylmethane-sulphonyi chloride, 20 μg./ml. leupeptin, 2 μg./ml. aprotinin and 80 mM β-glycerophosphate. After 10 minutes at 0° C., the lysate was centrifuged at 30,000 g for 10 minutes. The pellets were washed once by resuspension with the lysis buffer and subsequently centrifuged at 30,000 g. The supernatants were combined and centrifuged at 100,000 g. for 3 hours. The pellets were resuspended in 8M urea solution and boiled for 10 minutes. The extracts were analysed by one-dimensional SDS gel electrophoresis in 15% polyacrylamide gels (Laemmli, U.K., Nature, 227, 680–685/1970). After blotting the gel on to nitro-cellulose, the S6 protein was identified by the addition of anti-S6-antiserum.

EXAMPLE 2

Quercetin as inhibitor of protein kinase C

As was described in more detail in Example 1, the influence of quercetin on protein kinase C and on the multiplication of Walker carcinoma cells in culture was investigated. Quercetin was solubilised in dimethyl sulphoxide (DMSO). For the batch mixing, the solution in DMSO was made up to a DMSO end concentration of 1%. An equivalent amount of pure DMSO was added to the control groups. The influence of quercetin on the cell multiplication was investigated by the addition of the active material in DMSO to the culture medium up to an end concentration of 0.1%. The cells were cultured in the presence of the active material for 48 hours. The control group only received pure DMSO. 100% of the protein kinase C activity corresponds to 44.8 pmol/min. $^{32}$P transferred to Hl.

From the data obtained, it follows that quercetin functions as an inhibitor of protein kinase C (IC$_{50}$=25 μM).

EXAMPLE 3

Tamoxifen as inhibitor of protein kinase C

Analogously to the description in Example 2, the influence of tamoxifen on protein kinase C was investigated. From the data obtained, the IC$_{50}$ value could be determined as being 11.20 μM.

EXAMPLE 4

Staurosporin as inhibitor of protein kinase

Analogously to the description in Example 2, the influence of staurosporin on protein kinase C was investigated. The IC$_{50}$ value was determined as being 0.048 μM.

EXAMPLE 5

Ilmofosin as inhibitor of protein kinase C

Analogously to the description in Example 2, the effect of ilmofosin on protein kinase C was investigated. The IC$_{50}$ value was 20 μM.

EXAMPLE 6

ET-18-OCH$_3$ as inhibitor of protein kinase C

Analogously to the description in Example 2, the influence of ET-18-OCH$_3$ on protein kinase C was investigated. In the same way as ilinofosin, ET-18-OCH$_3$ inhibits protein kinase C (IC$_{50}$=24.8 μM).

EXAMPLE 7

General process for the determination of the synergistic effect of a combination of protein kinase C inhibitor and an anti-neoplastic active material.

a) Walker carcinoma cells from rats were cultured in suspensions of DMEM (Dulbecco's modified minimal essential medium) with a 10% portion (v/v) of horse serum and 25 mM MOPS buffer (pH 7.35 at 20° C.) at a temperature of 36.8° C. Dose-action curves for individual active materials or active material combinations were obtained by the addition of corresponding active materials to a suspension of Walker cells ($10^5$ cells/ml.). After an incubation time of 48 hours, the cells were counted with the help of an electronic counter (Coulter Electronics, Luton, U.K.). The multiplication of the cells (M) was calculated according to the following formula:

$$M=(T_{t-T0})/(C_{t-C0})*100,$$

in which C stands for the untreated control cells, T signifies the number of treated cells and the indices 0 and t indicate the number of the cells at the time point 0 and after 48 h.

The synergistic effect of the active material combination was determined by the method described by Chou and Talalay (Eur. J. Biochem., 115, 207–216/1981 and Advances Enzyme Regul., 22, 27–54/1984). The data used for the calculation originated from at least three different experiments. The calculation programme was obtained from Elsevier Biosoftware, Cambridge, U.K. (dose effect analysis with microcomputers).

b) [3H]-Thymidine incorporation.

The cytostatic or cytotoxic effect of the active materials or active material combinations on Meth A-fibrosarcoma cells was investigated in vitro on the basis of the reduced incorporation of [3H]-thymidine. The cells were suspended in DMEM, 10% FCS, 50 μM 2-mercaptoethanol, 100 U/ml. penicillin and 100 μg./ml. streptomycin up to an end concentration of $5\times10^4$/ml. in the absence of the active materials. The active materials were added to the cells in an end volume of 20 μl. Per concentration, 6 cultures of 0.2 ml. were used and incubated in microtitre plates in a moist atmosphere. The cultures were pulsed for 3 hours with 1 μCi (27 kBq/cell) [methyl-$^3$H]-thymidine (specific activity 5 Ci/mmol). The samples were subsequently collected and washed several times. The filter plates used were dried and transferred to scintillation test tubes. The radio-active incorporation was measured by the addition of Rotiscint.

EXAMPLE 8

Synergistic effect of quercetin and cis-diamminedichloroplatinum (II) (cis-DDP)

As described in Example 7a, the influence of cis-DDP, quercetin and a mixture of quercetin/cis-DDP (molar ratio 100:1) on Walker sarcoma cells from rats was investigated. The cells were cultured in the presence of the active materials in question for a period of 48 hours. The result is given in the following Table 1.

EXAMPLE 9

Synergistic combination of quercetin and mustargen

As described in Example 7a, the influence of quercetin, mustargen and a mixture of quercetin/mustargen (molar ratio 800:1) on Walker sarcoma cells from rats was investigated. The result is given in the following Table 1.

EXAMPLE 10

Synergistic combination of tamoxifen and cis-DDP

As described in Example 7a, the influence of tamoxifen, cis-DDP and a mixture of tamoxifen/cis-DDP (molar ratio 10:1) on Walker sarcoma cells from rats was investigated. The result is given in the following Table 1.

EXAMPLE 11

Synergistic combination of staurosporin and cis-DDP

As described in Example 7a, the influence of staurosporin, cis-DDP and a mixture of staurosporin/cis-DDP (molar ratio 1:100) on Walker sarcoma cells from rats was investigated. The result is given in the following Table 1.

EXAMPLE 12

Synergistic combination of ilmofosin and cis-DDP

As described in Example 7a, the influence of ilmofosin, cis-DDP and a mixture of ilmofosin/cis-DDP 5 (molar ratio 10:1) on Walker sarcoma cells from rats was investigated. The result is given in the following Table 1.

EXAMPLE 13

Synergistic combination of ET-18-OCH$_3$ and cis-DDP

As described in Example 7a, the influence of ET-18-OCH$_3$, cis-DDP and a mixture of ET-18-OCH$_3$/cis-DDP (molar ratio 10:1) on Walker sarcoma cells from rats was investigated. Similar to what was described in Example 12, in this case, too, a synergistic action was ascertained (see Table 1).

TABLE 1

Inhibition of the cellular replication and strengthening of the anti-proliferative effect of cis-DDP by inhibition of protein kinase C; summary of the IC$_{50}$ values

| inhibitor (example) | inhibition of the[1] protein kinase C IC$_{50}$ [μM] | cell proliferation IC$_{50}$ [μM] | IC$_{50}$ [μM][1] cell proliferation in combination with cis-DDP | nature[2] of the activity |
|---|---|---|---|---|
| quercetin (2,8,9) | 25 | 23 | 3.8 | synergism |
| tamoxifen (3,10) | 11.20 | 12.44 | 2.24 | synergism |
| staurosporin 4,11) | 0.048 | 0.4 | 0.004 | synergism |
| ilmofosin (5,12) | 0,56 | 20 | 2 | synergism |
| ET-18-OCH$_3$ (6,13) | 24.8 | 5.8 | 1.7 | synergism |
| cis-DDP | >1000 | 0.23 | — | — |

[1]By the IC$_{50}$ value is to be understood that concentration of the inhibitor at which a 50% inhibition of the protein kinase C or of the cell proliferation is reached.
[2]The calculation basis with regard to the synergistic effect took place according to the method of Chou and Talalay (Advances Enzyme Regul., 22, 27–54/1984).

EXAMPLE 14

The IC$_{50}$ values for a combination of ilmofosin with CDDP or doxorubicin were determined in the manner described above in Example 7b). The results obtained are shown in the following Table 2.

TABLE 2

Inhibition of tumour cell proliferation

| inhibitor PK-C A | anti-neoplastic active material B | ratio A:B | IC$_{50}$ [µg./ml.] |
|---|---|---|---|
| ilmofosin | CDDP | 100:1 | 1.09 |
| ilmofosin | doxorubicin | 100:1 | 1.11 |
| ilmofosin | — | — | 1.06 |

EXAMPLE 15

Preparation of pharmaceutical formulations

The compounds A and B selected as active materials can be used in various galenical formulations. The following Examples concern galenical compositions which contain an active material designated as A as protein kinase C inhibitor and an anti-neoplastic active material designated as B.

a) Tablets

| mixture I | | mixture II | |
|---|---|---|---|
| active material A | 50 mg. | active material B | 50 mg. |
| starch | 180 mg. | silicon dioxide | 100 mg. |
| magnesium stearate | 20 mg. | lactose | 100 mg. |
| | | Aerosil | 5 mg. |

Mixtures I and II are dry or moist granulated separate from one another. Subsequently, they are mixed with one another with the addition of 5 mg. talc and pressed into tablets.

b) Capsules

| mixture I | | mixture II | |
|---|---|---|---|
| active material A | 50 mg. | active material B | 200 mg. |
| lactose | 110 mg. | polyvinylpyrrolidone | 10 mg. |
| maize starch | 20 mg. | maize starch | 100 mg. |
| gelatine | 8 mg. | Ceetina HR | 10 mg. |
| magnesium stearate | 12 mg. | | |

Separately from one another, the two mixtures A and B are granulated in the usual manner. The two granulates are mixed with one another in a mixer in the given mixing ratio and the powder mixed in the mixer with talc. Subsequently, the mixture obtained is filled into hard gelatine capsules in a conventional machine.

c) Injection solutions (i.m. or i.v.)

An injection solution ready for intravenous (i.v.) injection contains:

active material A 50 mg.

active material B 100 mg.

sodium chloride 20 mg.

sodium acetate 6 mg.

distilled water ad 5 ml.

An injection solution ready for intramuscular (i.m.) injection contains:

active material A 100 mg.

active material B 100 mg.

benzyl benzoate 1 g.

injection oil 5 ml.

What is claimed is:

1. Process for preparing a synergistic pharmaceutical combination preparation with anti-neoplastic action, comprising the steps:

(a) determining the protein kinase C inhibition of a first active material which shows protein kinase C inhibition effect, wherein the determining is done by an assay of inhigition of protein kinase in vitro or inhibition or protein kinase in vivo;

(b) determining the synergistic effect of said first active material with a second active material having an anti-neoplastic action by measuring cell proliferation;

(c) identifying the combinations of said first active material and said second active material which have a synergistic antineoplastic effect; and (d) preparing a pharmaceutical preparation comprising said first active material and said second active material.

2. A process according to claim 1, wherein the second active material having anti-neoplastic activity is a lipid, lipid analogous, a cytostatic compound or a compound with phospholipase-inhibiting action.

3. A process according to claim 2, wherein the second active material having anti-neoplastic action is a cytostatic compound.

4. A process according to claim 3, wherein the cytostatic compound is an alkylant, a metal complex compound, an antimetabolite, an antibiotic, a hormone antagonist or a corticoid.

5. A process according to claim 3, wherein the cytostatic compound is cyclophosphamide, chlorambucil, cisdiamminedichloroplatinum (II), methotrexate, 5-fluorouracil, doxorubicin, bleomycin or tamoxifen.

6. A process according to claim 3, wherein the inhibitor of protein kinase C is quercetin, tamoxifen, ilmofosin, ET-18-OCH$_3$ or staurosporin.

7. A process according to claim 1, wherein the first active material is an inhibitor of protein kinase C selected from the group consisting of lipids, phospholipids, glycolipids, neutral lipids and O-alkyl and halogenated derivatives of neutral lipids.

8. A process according to claim 1, wherein the first active material is ilmofosin and the second active material is cis-diamminedichloreoplatinum (II).

9. The process of claim 1 wherein the inhibitor of protein kinase C is quercetin, ilmofosin, ET-18-OCH$_3$ or staurosporin.

10. A process for determining the synergistic activity of a combination neoplastic composition, comprising the steps:

(a) determining the protein kinase C inhibition activity of a first active material, wherein the determining is done by an assay of inhibition of protein kinase in vitro or inhibition of protein kinase in vivo;

(b) determining the synergistic effect of said first material with a second active material having antineoplastic action by measuring cell proliferation; and (c) and identifying the combinations which have a synergistic effect.

* * * * *